United States Patent [19]

Garin-Chesa et al.

[11] Patent Number: 5,437,865
[45] Date of Patent: Aug. 1, 1995

[54] ISOLATED SIALYLATED GLYCOPROTEIN ENDOSIALIN, WHICH IS EXPRESSED BY TUMOR ASSOCIATED VASCULAR ENDOTHELIUM

[75] Inventors: Pilar Garin-Chesa; Wolfgang J. Rettig; Lloyd J. Old, all of New York, N.Y.

[73] Assignee: Memorial Sloan-Kettering Cancer Center, N.Y.

[21] Appl. No.: 221,033

[22] Filed: Mar. 30, 1994

Related U.S. Application Data

[62] Division of Ser. No. 976,405, Nov. 13, 1992, Pat. No. 5,342,757.

[51] Int. Cl.$^6$ ............ A61K 39/00; C07K 14/00; C07K 14/435
[52] U.S. Cl. .................... 424/184.1; 514/8; 530/350; 530/395; 530/827
[58] Field of Search ............ 530/350, 387.7, 388.22, 530/395, 827; 536/23.5; 514/8; 424/184.1, 520

[56] References Cited

PUBLICATIONS

Rettig et al. PNAS 89: 10832–10836 (1992).
Ruiter et al. J. Invest Dermatol. 93: 255–325 (1989).
Schlingemann et al. Am. J. Pathol. 138: 1335–1347 (1991).
Seed et al. PNAS 84: 3365–3369 (1987).

*Primary Examiner*—David L. Lacey
*Assistant Examiner*—Phillip Gambel
*Attorney, Agent, or Firm*—Felfe & Lynch

[57] ABSTRACT

The invention is an isolated, sialylated glycoprotein, referred to as endosialin, which is expressed by tumor associated vascular endothelium and not normal vascular endothelium. The protein portion of the glycoprotein has a molecular weight of about 95 kilodaltons as determined by SDS-PAGE, and the glycoprotein has a molecular weight of about 165 kilodaltons, also as determined by SDS-PAGE. The oligosaccharides are linked by O-linkages to the protein. The glycoprotein is useful for making antibodies which are in turn used to identify tumor associated vascular endothelium.

4 Claims, 4 Drawing Sheets

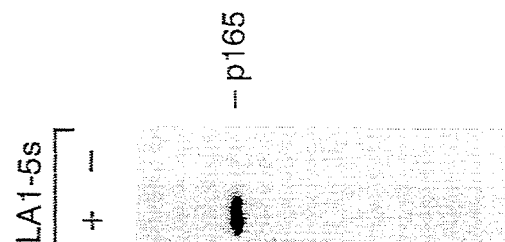
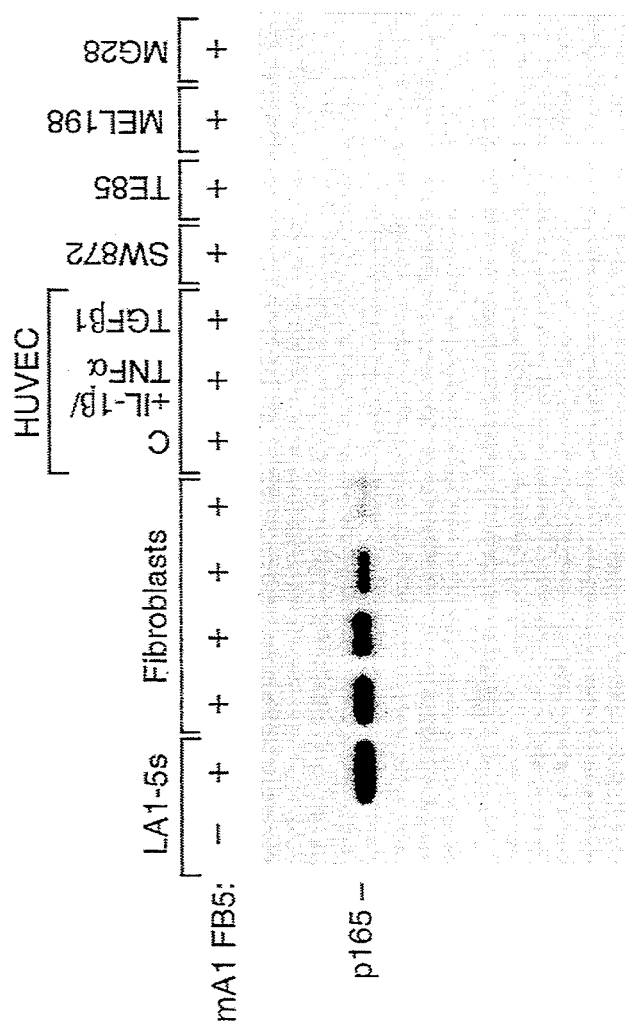
FIG. 2A
FIG. 2B

ISOLATED SIALYLATED GLYCOPROTEIN ENDOSIALIN, WHICH IS EXPRESSED BY TUMOR ASSOCIATED VASCULAR ENDOTHELIUM

RELATED APPLICATIONS

This application is a divisional of U.S. Patent Application Ser. No. 976,405, filed Nov. 13, 1992, which is now U.S. Pat. No. 5,342,757.

FIELD OF THE INVENTION

This invention relates to the fields of oncology and immunology. More particularly, it relates to monoclonal antibodies specific for tumor vascular endothelium, production of the monoclonal antibodies and the uses thereof.

BACKGROUND AND PRIOR ART

Carcinogenesis involves a series of somatic genetic changes affecting the structure and/or expression of oncogenes and tumor suppressor genes. Secondary genetic changes and epigenetic mechanisms may also be necessary to allow small nests of malignant cells to form clinically apparent primary and metastatic tumors. In the case of solid neoplasms, for example, it is well known that growth beyond diameters of 1-2 mm depends on formation of supporting stroma of newly formed blood vessels, usually accompanied by reactive stromal fibroblasts, lymphoid and phagocytic infiltrates, and extracellular matrix proteins. While cells of reactive tumor stroma are not transformed, they may differ from corresponding cells of normal tissues in proliferative activity, as well as in the expression of regulatory peptides, proteolytic enzymes, ECM proteins and cell surface antigens. Consequently these may provide additional targets for pharmacological and immunological investigations and interventions in cancer.

An example of such a target is the F19 cell surface glycoprotein, which is expressed in the reactive stroma fibroblasts of more than 90% of common epithelial cancers, including carcinomas of breast, colon, lung, bladder and pancreas, with little or no expression in normal adult tissues. The F19 cell surface glycoprotein and various teachings regarding it are found in Garin-Chesa et al., Proc. Natl. Acad. USA 87: 7235-7239 (1990); Rettig et al., Proc. Natl. Acad. Sci. USA 85: 3110-3114 (1988); and U.S. Pat. No. 5,059,523, all three disclosures hereby being incorporated by reference. In a recent, phase I study, it has been found that $^{131}$I labeled monoclonal antibody against F19 accumulates at tumor sites, thereby allowing tumor imaging in patients with hepatic metastases from colorectal carcinomas. See Welt et al., Proc. Am. Assoc. Cancer Res. 33: 319 (1992) regarding this imaging study.

Immunologic targeting of tumor vascular endothelial cells has not yet been accomplished, but is attractive for several reasons. One reason is that endothelial surface antigens are highly accessible to antibodies or antibody conjugates which circulate in the blood. Another reason is that the destruction or impairment of blood vessels associated with tumors would be expected to lead to widespread necrosis or arrest of growth of solid tumors. The activity of several antitumor agents, including tumor necrosis factor (TNF-$\alpha$), gamma interferon (IFN-$\delta$), and melphalan may result from vascular endothelial cell damage rather than direct tumor killing. See Old, Science 230: 630-632 (1985); Lienard et al., J. Clin. Oncol. 10: 52-60 (1992); Lejeune, Eur. Cytok. Net. 2: 124 (1992) for information on these studies.

The targeting of tumor vascular endothelial cells, discussed supra, requires the availability of a monoclonal antibody ("mAb") which is specific for these cells. While the field of immunology as it relates to production of monoclonal antibodies has made great strides since 1975 when Kohler & Milstein first succeeded in generating hybridomas, preparation of monoclonal antibodies with a desired cell type specificity is hardly simple or routine. For example, one must assume that an antigen of requisite specificity exists, or is expressed on the targeted cell, and this is not necessarily the case. This is essential for specificity in general, and is critical for vascular tissue, because any mAb which binds to vascular tissue generally rather than to tumor vascular endothelial cells specifically, will target normal vascular tissues, leading to obvious adverse consequences.

While mAbs to endothelial cells and to tumors originating therefrom are known, the art has not previously been aware of monoclonal antibodies which are specific to tumor vascular endothelium to the exclusion of other non-transformed cell types. Such monoclonal antibodies have, however, now been prepared, and the cell surface antigen to which they are directed has been identified, isolated, and characterized. These, as well as the ramifications thereof, are the subject of the disclosure which follows.

BRIEF DESCRIPTION OF THE FIGURES

FIG. 1(A) involves leiomyosarcoma, FIG. 1(B), renal cell carcinoma, FIG. 1(C) osteogenic sarcoma, and FIG. 1(D) colon carcinoma. The studies involved avidinbiotin immunoperoxidase staining, using hematoxylin counterstanding, and magnifications of 10×(1A), or 20×(B-D).

FIG. 2(A) depicts immunochemical analysis of the FB5 antigen (endosialin), using various cell types.

FIG. 2(B) is an immunoblot analysis of extracts of cell line LA1-5s.

DETAILED DESCRIPTION OF THE PREFERRED EMBODIMENTS

Example 1

Figure 1A:
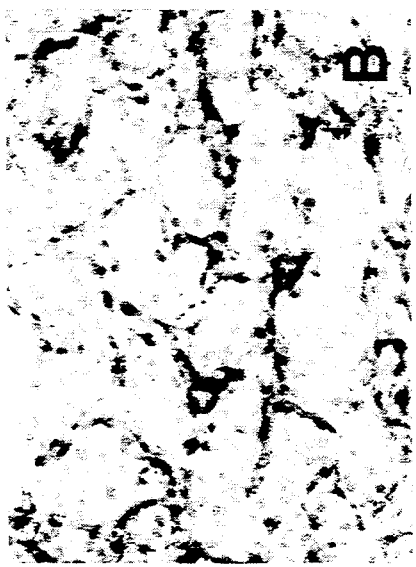
FIGS. 1(A), (B), (C) and (D) show studies of immunohistochemical staining to detect FB5 antigen (endosialin) in various tumor vascular endothelial cells.
Figure 1B:
Figure 1C:
Figure 1D:

Production of monoclonal antibody FB5 was carried out as follows. Immunogen was prepared by combining cultured human fetal fibroblasts in phosphate buffered saline, to a concentration of $2 \times 10^7$ cells/ml. The immunogen was administered to mice (strain (BALB/Cx-A)F1, via intraperitoneal injections (100 microliters). Four booster injections were administered, at 2-4 week intervals, using the same immunogen. Three days after the last immunization, the mice were sacrificed, and their spleens were removed and dispersed into single cell suspensions in RPMI 1640 media, following standard techniques. The spleen cells were then fused with HPGRT deficient X63-Ag8.653 mouse myeloma cells using polyethylene glycol (PEG), again following standard techniques.

The cells were then distributed in microculture plates, and grown in the presence of HAT medium, so as to select fused cells from non-fused cells.

Once cultures were established, their supernatants were screened using the well known mixed hemadsorption ("MHA") rosetting assay for antibodies reactive with immunizing cell type—i.e., cultured human fetal fibroblasts—but unreactive with a panel of epithelial cells (breast cancer, colon cancer, renal cancer), and neuroectodermal cell lines (melanoma, glioma).

Cells producing supernatant of desired reactivity were cloned using limiting dilution techniques. After each subcloning step, the supernatants were rescreened, using MHA. Four cycles were used to ensure isolation of a single hybrid clone.

Example 2

The protocol described supra was used to isolate hybridoma cell line FB5 and the mAb produced thereby. The mAb was then used in screening tests against a number of cell lines, normal tissue, and cancer samples. Determination of expression of the cell surface antigen to which FB5 bound was determined via mixed MHA rosetting assays, using serial 5-fold dilutions of the mAb (starting dilution: 20 ug/ml). The protocol used is described in Rettig et al., J. Immunol. 138: 4484–4489 (1987), and Rettig et al., Canc. Res. 45: 815–821 (1985). Table 1 sets forth these results.

TABLE 1

| FB5-positive | FB5-negative |
|---|---|
| Fibroblasts | Melanomas |
| WI-38, GM05387, | SK-MEL-13,SK-MEL,19,SK-MEL-23, |
| F135-35-18, Hs27, | SK-MEL, 178, SK-MEL, 198 |
| Hs68, FA537, SKF-AH | Gliomas |
| Neuroblastomas | U251MG, U343MG, U373Mg, SK-MG-28 |
| LA1-5s (control, boiled, NANasetreated), | Sarcomas |
| IMR-32, SMS-SAN, SMS-KAN | SW872, 8387, Saos-2, HT-1080, RD |
|  | Carcinomas |
|  | MCF-7, BT20, SK-RC-9, SK-RC-28, |
|  | Colo205, HCT15, HT-29, SK-OV6 |
|  | Leukemias |
|  | U937, HL-60, RAJI |
|  | Endothelial cells |
|  | HUVEC |
|  | activated HUVEC |

Several comments will assist in the interpretation of these data. First, the fibroblasts were derived from fetal (W1-38, GM05387, and F135-35-18), newborn (Hs27, Hs68), and adult (FA537, 3KF-AH) tissue, proving the target antigen's ubiquity on fibroblast cells.

For the neuroblastoma cell line LA1-5s, these were either tested untreated, or following treatment with neuraminidase (0.1 U/ml for 1 hour at 37° C.), or with boiling phosphate buffered saline for 5 minutes, following Rettig et al., J. Histochem. Cytochem. 37: 1777–1786 (1989).

The "HUVEC" cells were derived from different individuals, using passages 2–4. The activated HUVEC cells had been pretreated for 6 or 24 hours, with one of TNF$\alpha$ (50 ng/ml), IL-1$\beta$ (0.5 ng/ml), TGF-$\beta$1 (2 ng/ml), TPA (5 ug/ml), forskolin (50 mM), IFN-$\gamma$ (200 U/ml), bFGF (5–25 ng/ml), IL-4 (1 ng/ml), or IL-6 (20 ng/ml).

Cells were also tested for FB5 binding using immunoperoxidase staining, and/or immunoprecipitation assays. These assays permit detection of cell surface and intracellular antigens. Example 3, infra details the protocols used.

Example 3

Immunoprecipitation assays were carried out by labelling cells with a mixture of [$^{35}$S]-methionine and [$^{35}$S]-cysteine (Trans$^{35}$S labelled ICN; 40 $\mu$Ci/ml), for 18–24 hours, followed by extraction in a lysis buffer (0.01M Tris-HCl, 0.15M NaCl, 0.01M MgCl$_2$, 0.5% Nonidet P-40, 20 ug/ml aprotinin, and 2 mM phenylmethylsulfonyl fluoride). The lysates were then used for immunoprecipitation assays, followed by NaDodSO$_4$/-polyacrylamide gel electrophoresis and fluorography, following Rettig et al., Proc. Natl. Acad. Sci. USA 85: 3110–3114 (1988). Where desirable, purified antigens/-cell extracts were digested with neuramidase, endoglycosidase H, (25 mIU/ml), N-glycanase (10 U/ml), or O-glycanase (0.1 U/ml). Protein glycosylation inhibitors were also used, i.e., phenyl N-acetyl-$\alpha$-galactosaminide (5 mM), monensin (10 ug/ml), and tunicamycin (5 ug/ml).

When immunoperoxidase staining was used on fixed, permeabilized cells, mAbs at concentrations of 10–20 ug/ml were used, following Garin-Chesa et al., PNAS 87: 7235–7239 (1990), and Rettig et al., PNAS 85: 3110–3114 (1988).

Example 4

The immunoperoxidase methodology described supra was used to test a panel of normal adult tissues. These tissues were obtained from autopsy or surgical specimens, frozen in isopentane, precooled in liquid nitrogen and stored at −70° C. Five micron thick sections were cut, mounted on poly-L-lysine coated slides, air dried, and fixed in acetone (4° C., 10 minutes).

Bone marrow samples were tested differently, with cells being spun onto glass slides, and the assay being run using a streptavidin-alkaline phosphatase method.

The results are presented in Table 2, and indicate that all normal tissues tested were negative.

TABLE 2

| Organ system | FB5-negative normal tissues |
|---|---|
| Nervous system | Cerebral cortex, cerebellum, spinal cord, peripheral nerves |
| Endocrine system | Adrenal gland, thyroid gland, pancreas |
| Urinary system | Kidney, urinary bladder, prostate |
| Reproductive system | Testis, ovary, uterus |
| Digestive tract | Esophagus, stomach, small and large intestine, liver, pancreas |
| Pulmonary system | Lung, bronchus, trachea |
| Cardiovascular system | Heart, arteries, veins, capillaries, lymphatics |
| Lymphoid organs | Thymus, spleen, lymph node |
| Hematopoietic system | Bone marrow |
| Skin | Epidermis, dermis, appendages |
| Breast | Mammary gland |
| Connective tissues | Skeletal muscle, visceral and vascular smooth muscle, adipose tissue, cartilage |

Example 5

In view of the results obtained for cell lines and normal tissue, a panel of human tumors was tested using the same methodology as was used to test normal cells.

Antigen was detected in the endothelial cells of tumor blood vessels. These results are presented in Table 3, in the form "A/B", with "A" indicating the number of samples showing positive phenotype for vascular end cells and "B" the number of different samples tested. Abbreviations used are as follows: ASPS-alveolar soft part sarcoma; PNET-primitive neuroectodermal tumor; MPNT-malignant peripheral nerve sheath tumor.

TABLE 3

| Tumor type | FB-5+ phenotype |
|---|---|
| Carcinomas | |
| Renal cancer | 6/9 |
| Breast cancer | 8/12 |
| Colon cancer | 4/5 |
| Pancreas cancer | 3/5 |
| Lung cancer | 3/4 |
| Mesothelioma | 2/2 |
| Sarcomas | |
| Leiomyosarcoma | 5/9 |
| Osteogenic sarcoma | 7/12 |
| Chondrosarcoma | 5/8 |
| Fibrosarcoma | 4/6 |
| ASPS | 2/2 |
| Rhabdomyosarcoma | 6/8 |
| Ewing's sarcoma | 6/7 |
| Synovial sarcoma | 6/9 |
| Neuroectodermal tumors | |
| PNET | 4/4 |
| MPNT | 8/12 |
| Neuroblastoma | 2/3 |
| Melanoma | 3/5 |
| Glioma | 1/1 |
| Lymphomas | 0/5 |

In contrast to the results obtained with normal tissues where blood vessels are negative for the antigen, a high proportion of tumors showed expression of the target antigen in vascular endothelial cells. With respect to tumor vasculature, expression was confined to small blood vessels, primarily capillaries, and not on endothelium of large tumor vessels. The number of vessels showing the antigen varied, from small subsets to virtually the entire capillary bed in a given tumor. There was no discernable parameter which distinguished high expression from low expression.

Example 6

The expression of the antigen on neuroblastoma cell lines and cultured fibroblasts in vitro afforded a ready source for biochemical analysis. The immunoprecipitation protocol set forth in example 2, supra, was carried out on cell types LA1-5s (neuroblastoma), F135-35-18, W1-38, FA-334 and GM01398 (fibroblasts), "HUVEC" (human umbilical cord endothelial cells), a leiomyosarcoma cell line (SW872), an osteosarcoma (TE85), a melanoma (SK-MEL-198), and a glioma (SK-MG-28). FIG. 2A shows that in the immunoprecipitation studies, the antigen migrated as a 165 kd band on NaDodSO$_4$/PAGE.

Immunoblot studies were also carried out, using cell line LA1-5s extracts, employing the alkaline phosphatase detection system of Fellinger et al., Cancer Res. 51: 336-340 (1991). These results, presented in FIG. 2B, also show a 165 kd target antigen.

Example 7

Figure 2C:
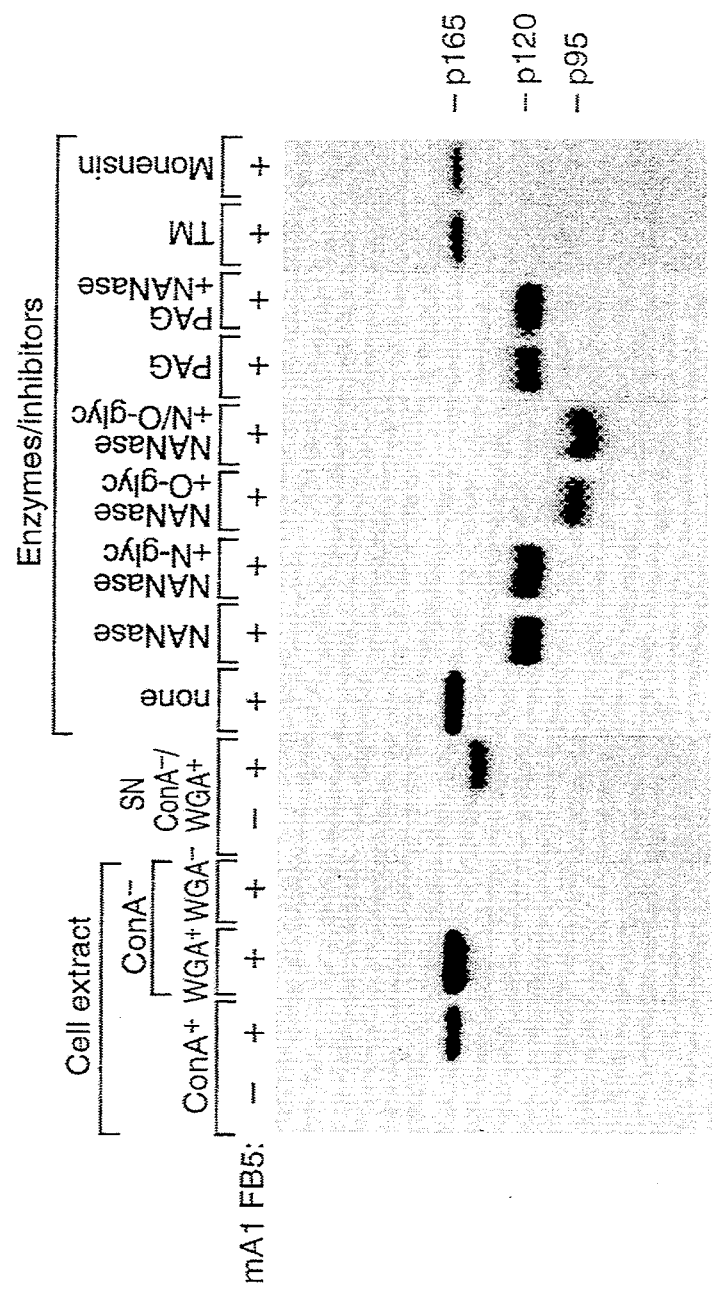
FIG. 2(C) shows lectin binding and carbohydrate analysis of FB5 antigen (endosialin).

Following the studies set forth supra, enzymatic digestion and metabolic inhibition studies were carried out, using the panel of enzymes described supra. FIG. 2C shows these results. One concludes from these studies that the 165 kd antigen is composed of a 95 kd core polypeptide, with abundant, highly sialylated O-linked oligosaccharides. This can be seen in the results obtained using neuraminidase (a desialylated 120 kd protein), and the generation of a 95 kd protein following combined treatment with neuraminidase and O-glycanase. The enzymes endoglycosidase H and N-glycanase had no effect on the antigen. Tunicamycin, which blocks N-linked glycosylation, and monensin, which interferes with Golgi apparatus protein processing, also did not impact the molecule. Similarly, when 5 mM phenyl-α-GalNAc was added to cells, the resulting molecule was a 120 kd protein species. The added molecule is a putative inhibitor of O-glycosylation but its precise mode of action is unknown. (Kuan et al., J. Biol. Chem. 264: 19271-19277 (1989)).

Example 8

Further studies were carried out to investigate the lectin binding pattern of the molecule. In these experiments, tests were carried out to determine whether the native and unglycosylated molecules bind to wheat germ agglutinin, as such binding would confirm the presence of sialic acid in the glycosylation of the molecule. To test this, Trans$^{35}$S labeled LA1-5s cell extracts and cell free culture supernatants were applied to wheat germ agglutinin (WGA SEPHAROSE), Concanavalin A SEPHAROSE ("Con A") using 250 mM α-D-methyl mannopyranoside as an eluting agent for Con A studies, and 250 mM galactosamine for WGA (SEPHAROSE in a registered trademark applied to high molecular weight substances used in gel filtration). FIG. 2C shows the results of the experiments. The native antigen binds to WGA-Sepharose, whereas antigen desialylated as above, does not. Partial binding to Con A Sepharose was observed for the native antigen.

Example 9

Figure 3:
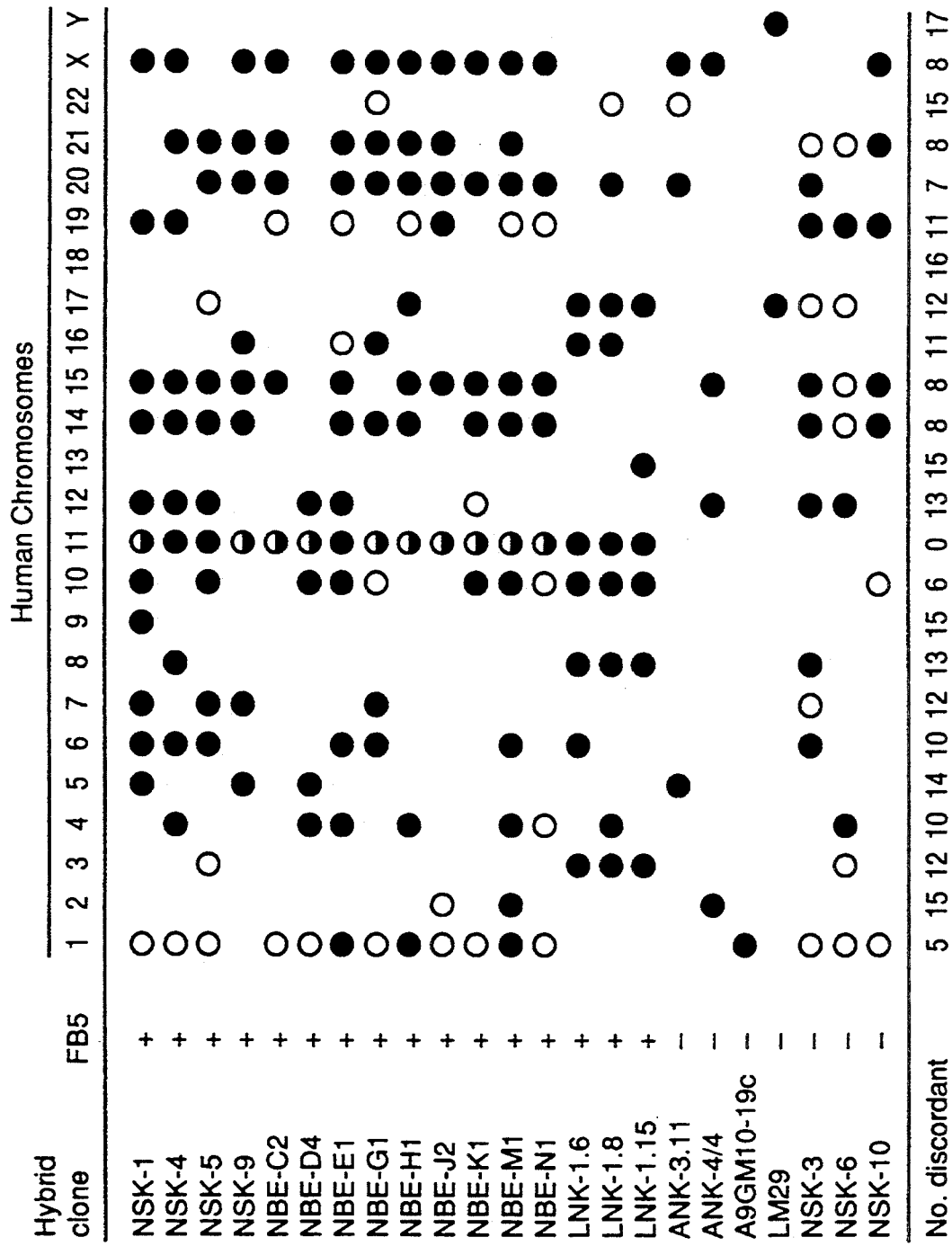
FIG. 3 summarizes studies leading to the assignment of the gene for FB5 antigen (endosialin) to a specific chromosome fragment.

Studies were carried out to determine the chromosomal location of the genes coding for the antigen bound by FBS. Serological analysis of a panel of rodent-human hybrids was carried out, following, e.g., Rettig et al., J. Immunol. 138: 4484-4489 (1987); Rettig et al., PNAS 81: 6437-6441 (1984); Rettig et al., Genomics 6: 176-183 (1991). The cells chosen for analysis were hybrids derived from FB5+ human neuroblastoma cells and murine FBS− neuroblastoma cells. The hybrids contain different portions of the human chromosome complement. Analysis of these data according to, Rettig et al., Proc. Natl. Acad. Sci. USA 81: 6437-6441 (1984), and as presented in FIG. 3, lead to the conclusion that the pertinent antigen is coded for by human chromosomal region 11q13-qter. Such analyses are art routine and require no further explanation.

The foregoing shows the production of monoclonal antibodies which specifically bind to vascular endothelium of cancer tissues, to the exclusion of other normal cells. These monoclonal antibodies also bind to samples of sarcoma tissues, thereby making them available for various uses in connection with sarcoma. In the discussion which follows, whereas tumor vascular endothelium is stressed, it should be borne in mind that diagnosis, monitoring and treatment of sarcoma is also encompassed by the invention. Thus, one aspect of the invention is a monoclonal antibody which specifically binds to vascular endothelium of tumors, and the hybridomas which produce these monoclonals. In a particular preferred embodiment, the hybridoma cell line is cell line FB5, and the monoclonal antibody produced thereby. This cell line has been deposited in accordance with the Budapest Treaty, and has been assigned Accession Number ATCC HB11190 at the American Type Culture Collection, 12301 Parklawn Drive, Rockville, Md. 20852. This deposit was made on Nov. 12, 1992. In a particular preferred embodiment, the monoclonal antibody is one which specifically binds to a sialylated glycoprotein having a molecular weight of about 165 kilodaltons as determined by SDS-PAGE, wherein said antigen is found on vascular endothelium associated with a tumor. It is to be pointed out, as shown supra, that the molecule, referred to hereafter as "endosialin", may be modified with the monoclonal antibodies of the invention still binding thereto. Such modifications include, e.g., partial or total sialylation.

When "monoclonal antibody" is used herein, it is to be understood that this is not limited to those monoclonal antibodies directly produced by hybridomas. The term is meant to incorporate, e.g., the well known binding fragments of monoclonal antibodies such as the Fab, F(ab)$_2$ and other binding fragments, oligomeric or polymeric constructions including a plurality of the monoclonals complexed to each other, chimeric monoclonal antibodies which contain immunoglobulin segments from two or more species (e.g., human and mouse), recombinant monoclonal antibodies, humanized materials, and so forth. Additionally, the term embraces the monoclonal antibodies produced by human B cells which have not been fused to myeloma, but have been rendered culturable in other ways, such as via transformation of human B cells with Epstein Barr Virus ("EBV"), or other transforming means.

The antibodies of the invention can clearly be used in diagnostic methods to identify the site of vascular endothelium associated with a tumor, whereby the monoclonal antibody is contacted to a sample to be assayed, and its binding is monitored. Such binding can be determined using any of the standard immunoassay protocols known to the artisan, including, but not being limited to, radioimmunoassays, enzyme linked immunosorbent assays, sandwich assays, competitive assays, and so forth. Many of these assays require the use of a detectable label which is attached to the antibody, and any of the labels known to the art, including radioactive, chromophoric, fluorophoric, enzymatic, magnetic, and metallic particles may be used. In carrying out the assays, the sample of interest may be, e.g., a tissue sample or body fluid sample. Further, the specificity of the mAb permits the artisan to use it in in vivo diagnosis, in a manner not unlike that described by Welt et al, supra. Among the varieties of in vivo diagnosis which can be used, radioimaging is particularly preferred.

The ability of the monoclonal antibodies of the invention to target, e.g., tumor associated vascular endothelium makes them particularly useful in a therapeutic context. The vascular bed of tumors, as is the case with any vascular bed, is responsible for nourishing its associated tissue. Thus, an anti-tumor therapy is envisaged as part of this invention. This therapy comprises administering an amount of the monoclonal antibodies of the invention in a manner sufficient to inhibit proliferation of the tumor or to actually cause necrosis thereof. Either inhibition or necrosis is provoked by combining the monoclonal with an appropriate agent having inhibitive or necrotic effect on the tumor. Such agents include, e.g., those that inhibit circulation of blood to the tumor, such as clot forming agents, including the clot forming enzymes of the well known coagulation cascade. Other agents which destroy cells, and therefore would destroy the vascular endothelium associated with the tumor, include all cytotoxic agents such as mitomycin c, metal containing compounds, enzymes, ricin chains, radioisotopes, and so forth. Any of these agents may be complexed to the mAbs in a manner well known to the art. The mAbs therefore serve as carriers for targeted cell destruction. In addition, they may be used in connection with liposomal delivery systems, where the liposome contains the inhibiting or necrotizing agent, and the mAbs target these to the site of the vascularization. Further, by modifying the mAbs so as to retain their specificity but to also be complement fixing or inflammatogenic one may use the modified form of mAbs per Se without a second agent. The complement fixing or inflammatogenic form of the mAb provokes an in vivo response in the subject, this response leading to destruction of the targeted cells.

The monoclonals, either alone or with the various materials described supra, may be formulated in various reagent formats. For example, the mAb, "as is", or in complement fixing or inflammatogenic form, can be combined with a pharmacologically acceptable carrier. When used in connection with the various materials disclosed herein, these can be attached to the mAb to form a conjugate, the conjugate then being combined with a pharmacologically acceptable carrier. It is also possible to prepare a kit type of reagent, wherein the mAb and the second substance are presented in separate portions, both of which are included in a container means.

In a particularly preferred embodiment of the invention, the new mAbs described herein are combined with a second mAb. Preferably, this second mAb is one which binds directly to tumor cells or to reactive stroma fibroblasts of tumors, an example being mAb F19, discussed supra. This second mAb may also be formulated in any of the ways the new mAbs are formulated (e.g., conjugated, treated to be complement fixing-/inflammatogenic, etc.).

When "monoclonal antibody" is used herein, the term refers not only to the whole mAb, but also to those fragments which retain the binding specificity described herein, such as, but not being limited to, Fab fragments. Also encompassed are all chimeric and bifunctional forms of the mAb, it having been well established that any portion of the mAb having specificity for the target antigen may be combined with portions of other monoclonal antibody molecules. These other molecules may be, e.g., antibodies obtained from other species (human or other primates, as well as rodent species). These chimeric mAbs are desirably manufactured so as to impart cytotoxic activity to the resulting hybrid or bifunctional antibody.

An example of such a construct is one where the reshaped or reconfigured mAb possesses both a binding domain typical of FB5 and an attachment site for T cells or macrophages. This results in a mAb with dual binding properties, and the mAb may provoke the cascade of events associated with a T cell or macrophage response to the cells to which the mAb is bound, and a secondary immune response against adjacent cells.

As indicated supra, any of the foregoing formulations are useful not only for the purposes of identifying tumor vascular endothelium and in targeted therapy, but in parallel approaches for sarcoma.

The invention also describes an isolated glycoprotein molecule characteristic of tumor associated vascular endothelium. This molecule, in native, glycosylated form has a molecular weight of about 165 kilodaltons as determined by SDS-PAGE, a 95 kilodalton portion thereof serving as the protein "core" of the molecule. The molecule, referred to herein as endosialin, is itself useful as an immunogen for securing mAbs of the specificity described herein, and as a vaccine for generation of protective mAbs. The vaccine includes an effective amount of the described surface antigen endosialin, and any of the pharmaceutically acceptable adjuvants well known to the art and used in vaccine formulations.

Localization of the gene for the protein portion of endosialin to a specific arm of a human chromosome, as described supra, facilitates identification and isolation of a nucleic acid sequence coding therefor. Other aspects of the invention will be clear to the skilled artisan and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated, sialylated glycoprotein expressed by vascular endothelium associated with a tumor and not normal vascular endothelium, wherein said sialylated glycoprotein is specifically bound by monoclonal antibody produced by hybridoma cell line ATCC 11190, has a molecular weight of about 165 kilodaltons as determined by SDS-PAGE, the protein portion of said glycoprotein have a molecular weight of about 95 kilodaltons as determined by SDS-PAGE, are oligosaccharides being linked thereto by O-linked glycosylation.

2. Isolated protein having a molecular weight of about 95 kilodaltons as determined by SDS-PAGE, wherein said protein is the protein portion of the isolated, sialylated glycoprotein expressed by vascular endothelium associated with a tumor and not normal vascular endothelium wherein said sialylated glycoprotein is specifically bound by monoclonal antibody produced by hybridoma cell line ATCC 11190, has a molecular weight of about 165 kilodaltons as determined by SDS-PAGE.

3. Immunogenic composition comprising the isolated, sialylated glycoprotein of claim 1, and an adjuvant.

4. Immunogenic composition comprising the isolated protein of claim 2, and an adjuvant.

* * * * *